United States Patent [19]
Kameda et al.

[11] Patent Number: 5,923,018
[45] Date of Patent: Jul. 13, 1999

[54] MEDICAL CARE SCHEDULE AND RECORD AIDING SYSTEM, MEDICAL CARE SCHEDULE AND RECORD AIDING METHOD, AND PROGRAM STORAGE DEVICE READABLE BY THE SYSTEM

[75] Inventors: Toshitada Kameda; Tomio Itoh, both of Kamogawa, Japan

[73] Assignee: Kameda Medical Information Laboratory, Japan

[21] Appl. No.: 08/910,006

[22] Filed: Aug. 12, 1997

[30] Foreign Application Priority Data

Jan. 31, 1997 [JP] Japan .................................. 9-018172

[51] Int. Cl.$^6$ ...................................................... G06F 17/00
[52] U.S. Cl. ............................ 235/385; 235/492; 395/203
[58] Field of Search ..................................... 235/379, 380, 235/381, 383, 385, 492; 902/216; 395/202, 203

[56] References Cited

U.S. PATENT DOCUMENTS

| | | | |
|---|---|---|---|
| 5,307,262 | 4/1994 | Ertel ............................................ | 705/2 |
| 5,590,038 | 12/1996 | Pitroda ..................................... | 235/380 |
| 5,682,027 | 10/1997 | Bertina et al. ........................... | 235/380 |
| 5,705,977 | 1/1998 | Jones ..................................... | 340/457.2 |
| 5,719,780 | 2/1998 | Holmes et al. ..................... | 364/479.01 |

FOREIGN PATENT DOCUMENTS

| | | |
|---|---|---|
| 59-83265 | 5/1984 | Japan . |
| 62-245373 | 10/1987 | Japan . |
| 2-22769 | 1/1990 | Japan . |
| 4-229368 | 8/1992 | Japan . |
| 4-333973 | 11/1992 | Japan . |
| 5-108677 | 4/1993 | Japan . |
| 5-216903 | 8/1993 | Japan . |
| 5-314150 | 11/1993 | Japan . |
| 6-83880 | 3/1994 | Japan . |
| 6-218011 | 8/1994 | Japan . |

OTHER PUBLICATIONS

Harutoshi Yamaguchi, *Innovation of Management of Hospital by United Medical Information System*, published in IE review No. 196, vol. 37, No. 3, published by Japanese Industrial Engineering Association, Aug. 1, 1996, pp. 18–24.

Toshitada Kameda, *Validity of Medical Information System and its Effect*, published in Progress of Medicine, Life Science Medical, Apr. 10, 1996, pp. 14–19.

(List continued on next page.)

*Primary Examiner*—Donald Hajec
*Assistant Examiner*—Drew A. Dunn
*Attorney, Agent, or Firm*—Finnegan, Henderson, Farabow, Garrett & Dunner, L.L.P.

[57] ABSTRACT

A medical care schedule and record aiding system is provided with: a plurality of frame definition files each storing frame definition data to define a frame of a table, in which medical care actions of various types are arranged in first rows for each type of the medical care actions and in second rows orthogonal to the first rows for each date; a plurality of cell definition files, which are set for each of the frame definition files, and each of which stores cell definition data including at least positional data, which indicates a first row and a second row of each of cells segmented by the frame of the table, among (i) the positional data, (ii) a medical care category code, which corresponds to each of cells from among a plurality of medical care category codes respectively assigned to the medical care actions of various types in advance, and (iii) text data indicating a text to be displayed in each of cells; and a master file for storing a plurality of medical care action appellation data, each of which indicates an appellation of a medical care action corresponding to respective one of the medical care category codes, in association with each of the medical care category codes; a frame selection device for selecting an arbitrary one of the frame definition files; a display data generation device for generating frame display data and cell content display data; and a display device for displaying the table on the basis of the generated display data.

15 Claims, 9 Drawing Sheets

OTHER PUBLICATIONS

Katsuhiro Ohashi, *Dairy Medical Examination by Use of Electronic Chart*, published in Progress of Medicine, vol. 169, No. 12, published by Medical and Dental Medicine Publishing Company, Jun. 18, 1994, pp. 1187–1190.

Ikuyo Yoshida, *Medicine is Changed by Making a Chart into Electronic One*, published in Database System 1996, vol. 2, No. 9, Sep. 1, 1996, pp. 68–72.

FIG.4

| | 12-13-94(TUES) 1ST DAY(CCU) | 12-14-94(WED) 2ND DAY(CCU) | 12-15-94(THUR) 3RD DAY(CCU) | 12-19-94(MON) 7TH DAY |
|---|---|---|---|---|
| RECORD | NURSING SCHEDULE | | | |
| ACTIVITY RESTRICTION (REST/EXCRETION/ CLEANNESS) | BED BATH PUDIC CLEAN WASH HELPER | BED BATH PUDIC CLEAN WASH HELPER | BED BATH | BED BATH |
| MEAL | | MORNING: △ LUNCH: ○ DINNER: □ | | ORDINARY MEAL |
| PRACTICE/ MONITOR | VITAL SIGN WEIGHT MEASUREMENT SG CATHETER MONITOR CARDIOGRAM PULSE OXIMETER | VITAL SIGN WEIGHT MEASUREMENT | VITAL SIGN WEIGHT MEASUREMENT | VITAL SIGN WEIGHT MEASUREMENT |
| TEST | CARDIOGRAM BREAST X RAY CPK, CPK-MB 24 HOURS FECALURIA | CARDIOGRAM BREAST X RAY CPK, CPK-MB 24 HOURS FECALURIA | CARDIOGRAM BREAST X RAY CPK, CPK-MB 24 HOURS FECALURIA | CARDIOGRAM BREAST X RAY |
| ORAL MEDICINE/ EXTERNAL MEDICINE | | TIMELY ADMINISTRATION ① | TIMELY ADMINISTRATION ① | TIMELY ADMINISTRATION ① |
| INJECTION | INSTILLATION | INSTILLATION | INSTILLATION | |
| TREATMENT | MT EVULSION S-G EVULSION DIV DELETION, WPAPPING NEBLIZER, SPIRON | A LINE EVULSION B CATH EVULSION NEBLIZER SPIRON | Y-DRAIN EVULSION NEBLIZER SPIRON | NEBLIZER SPIRON |

FIG. 5

| 12-09-94 (Fri) | [HOSPITALIZATION 3rd DAY]

◇DOCTOR'S RECORD
　・OPERATION/SURGERY ORDER
◇EVALUATION
　○VITAL SIGN
　○WEIGHT MEASUREMENT
◇MEDICATION
　○06:00　HEPARIN　3000UNITS　DIV
　○12:00　HEPARIN　3000UNITS　DIV
　○18:00　HEPARIN　3000UNITS　DIV
　○24:00　HEPARIN　3000UNITS　DIV
　○TIMELY MEDICATION
　　　: INDERAL TABLET 10mg 3TABLETS
　　　　POSTCIBAL MORNING LUNCH DINNER(UNTIL12.12)

◇TEST
　◎URINE GENERAL TEST
　◎URINE CHEMICAL TEST : CCr
　◎BLOOD SUGAR BURDEN TEST : TRETMENT
　◎15:30　　CC-T　　　　　(RESERVATION AT HOSPITALIZATION)
　◎PM oncall CAROTID ECHO(RESERVATION AT HOSPITALIZATION)
◇MEAL
　○MEAL INDICATION
　　　: CARDIAC NORMAL FOOD 1600Cal NaCl5g
◇REST/EXCRETION/CLEANNESS
　○SHOWER

FIG. 6

|  | 12-07-94 (Wed)<br>UPON<br>HOSPITALIZING | 12-08-94 (Thur)<br>2nd DAY OF<br>HOSPITALIZING |
|---|---|---|
| MEAL | CARDIAC<br>NORMAL FOOD | CARDIAC<br>NORMAL FOOD |
| TEST | 3 KINDS CULTURE | 9:00 CARDIOGRAM<br>10:00 BREAST X RAY<br>12:00 ANTIBODY TEST<br>15:00 IMA ECHO |

| | '95 March<br>2 MONTHS<br>LEAVING<br>HOSPITAL | '95 April<br>3 MONTHS<br>LEAVING<br>HOSPITAL | '95 May<br>4 MONTHS<br>LEAVING<br>HOSPITAL |
|---|---|---|---|
| MEDICATION | TIMELY<br>MEDICATION | TIMELY<br>MEDICATION | |
| TEST | March 4th<br>CARDIOGRAM<br>March 18th<br>CARDIOGRAM | April 15th<br>CARDIOGRAM | May 15th<br>CARDIOGRAM |

40
41

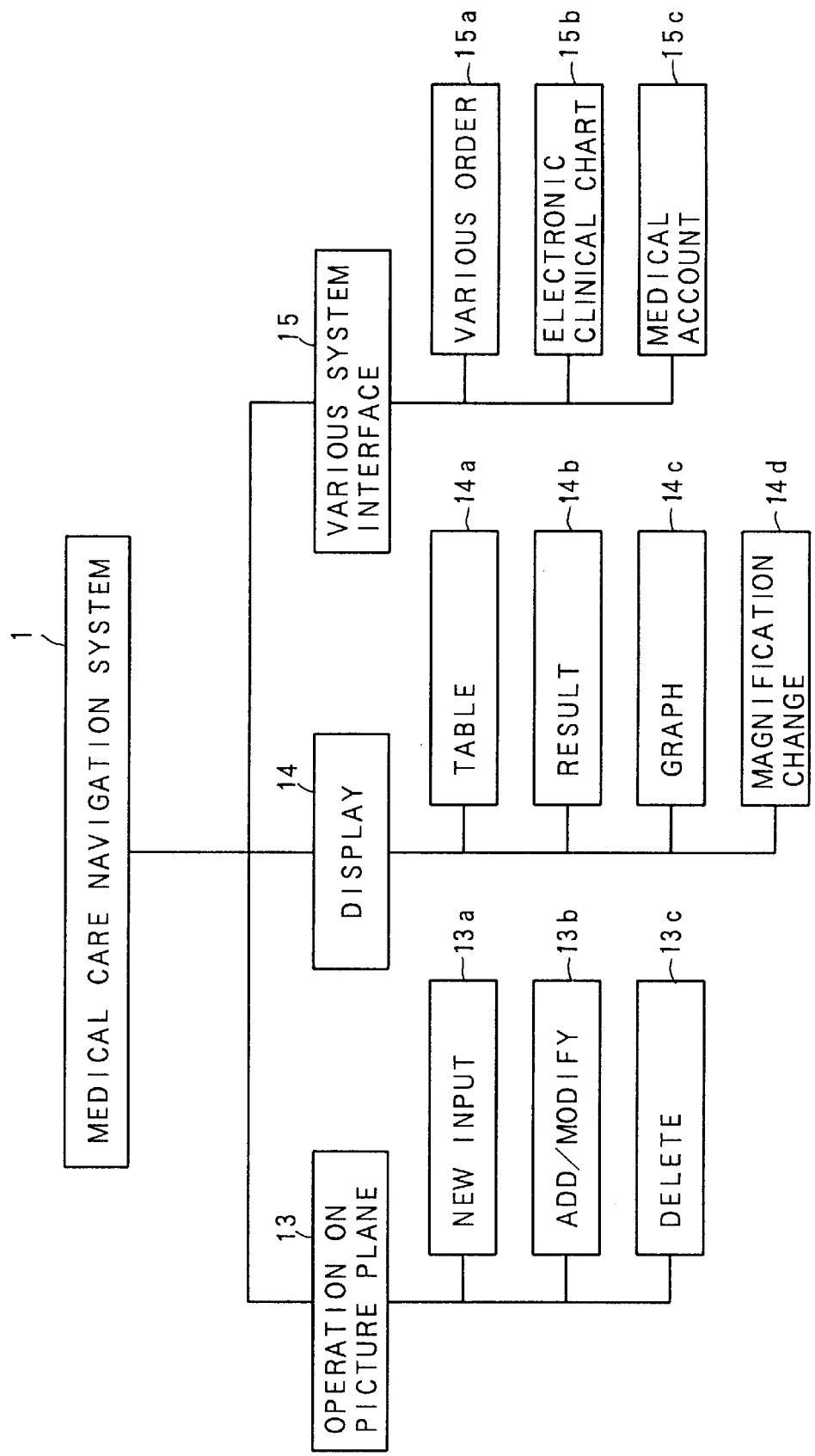

MEDICAL CARE SCHEDULE AND RECORD AIDING SYSTEM, MEDICAL CARE SCHEDULE AND RECORD AIDING METHOD, AND PROGRAM STORAGE DEVICE READABLE BY THE SYSTEM

BACKGROUND OF THE INVENTION

1. Field of the Invention

The present invention generally relates to a technical field of managing, storing, processing, inputting and outputting the medical care information, and more particularly to a technical field of a new system for aiding or navigating a person related to medical care such as a medical doctor, a nurse, a pharmacist, a medical office worker and so on, to make up a better medical care schedule and record.

2. Description of the Related Art

Conventionally, each medical doctor, nurse, etc. makes up the medical care schedule as for medical care actions such as a test, an examination, an inspection, a reservation for hospitalizing, an operation, a medication and so on, by thinking and summarizing it in his or her mind on the basis of his or her experience and sense. For example, a medical doctor may make it up by writing, on a so-called "instruction table" sheet for exclusive use, the medical care schedule or plan for a certain patient such as the schedule and content of the test and the medication, the schedule and content of the medical operation, the schedule and content of the post-operation treatment or examination and so on. In such a case, it is general that a standard date for the medical care schedule, such as a date two days before the medical operation, the date of hospitalization or the like, is written on this instruction table sheet by the medical doctor. Therefore, a better medical care schedule can be made up by a well trained medical doctor etc., who thinks it carefully.

On the other hand, as a system for processing medical information by use of a computer, there is a computer system for medical office work, to which data indicating types of medical examination, medication, medical insurance, etc. are inputted and which speedily calculates the medical reward out of those inputted data and outputs a bill. Under the development of the computer communication technique nowadays, an order system is also proposed which quickly transmits the computer readable information in place of a paper chit on which the message is written, from one terminal device at one department to the other terminal device at the other department so as to speed up the preparation of the medicine, the account and the like.

Since the medical care schedule is related to a human life and thus very important, it is desirable to standardize the medical care schedule to some extent and keeps its quality high regardless of the discretion or skill of the individual doctor.

However, first of all, the aforementioned medical care schedule, which is made up by each doctor, nurse, etc., needs a work to summarize it in his or her mind in such a way as "the prescription will be performed on X day, the test will be performed on Y day, . . . " for example, which basically cannot function as a schedule table related to the medical care actions or processes. And, above all, this kind of conventional medical care schedule depends very much upon the individual discretion and skill of each doctor, nurse, etc., so that it is almost impossible to schedule and program the medical care processes which are the objectively best in case of serving various medical care actions and processes with respect to numbers of patients who have various kinds of chronic and disease, under the complication and the high development of the medical technique nowadays. As a result, there is a serious problem that a less effective medical treatment may be applied by an erroneous judgment of the doctor, the nurse, the pharmacist or the like, and that the chronic or disease, which would have been cured by applying the most suitable treatment, is not finally cured.

On the other hand, according to the aforementioned method of manually writing the medical care schedule on the "instruction table" sheet for exclusive use, it is very inconvenient to change the schedule or plan at the presence of an emergent hospitalization of another patient, or in case of changing the future schedule on the basis of the results of some test or examination, for example.

Further, the quality itself of the medical care can be hardly improved by the aforementioned computer system for the medical office work and the order system, although the burden on the office works and the waiting time of the patients can be reduced by those systems.

SUMMARY OF THE INVENTION

It is therefore an object of the present invention to provide a medical care schedule and record aiding system, a medical care schedule and record aiding method and a program storage device readable by the system, which can aid or navigate the staff related to the medical care to make up an appropriate and objective medical care schedule and record toward the best medical care for each patient.

The above object of the present invention can be achieved by a medical care schedule and record aiding system provided with: a plurality of frame definition files each storing frame definition data to define a frame of a table, in which medical care actions of various types are arranged in first rows for each type of the medical care actions and in second rows orthogonal to the first rows for each date; a plurality of cell definition files, which are set foreach of the frame definition files, and each of which stores cell definition data including at least positional data, which indicates a first row and a second row of each of cells segmented by the frame of the table, among (i) the positional data, (ii) a medical care category code, which corresponds to each of cells from among a plurality of medical care category codes respectively assigned to the medical care actions of various types in advance, and (iii) text data indicating a text to be displayed in each of cells; a master file for storing a plurality of medical care action appellation data, each of which indicates an appellation of a medical care action corresponding to respective one of the medical care category codes, in association with each of the medical care category codes; a frame selection device for selecting an arbitrary one of the frame definition files; a display data generation device for (i) generating frame display data to display the frame of the table on the basis of the frame definition data stored in the selected frame definition file, (ii) specifying each cell corresponding to respective one of the cell definition files on the basis of the positional data in the cell definition data stored in each of the cell definition files set for the selected frame definition file, (iii) developing the medical care category code, which is included in the stored cell definition data, to the medical care action appellation data, which correspond to the medical care category code to be developed, with referring to the master file, and (iv) generating cell content display data to be displayed in the specified each cell on the basis of the developed medical care action appellation data and the text data; a display device for displaying the table on the basis of the generated frame display data and the generated cell content display data; a cell selection device for selecting an arbitrary one of the cells constructing the displayed table; an input device for newly inputting, adding, changing, modifying or deleting the cell content display data on the display device as for the cell selected by the cell selection device; and an update device for updating the cell definition file specified on the basis of the positional data of the selected cell, when the cell content display data is newly inputted, added, changed, modified or deleted by the input device, in correspondence with the newly inputted, added, changed, modified or deleted cell content display data.

According to the system of the present invention, each of the frame definition files stores the frame definition data to define the frame of the table, in which medical care actions of various types are arranged in first rows for each type of the medical care actions and in second rows orthogonal to the first rows for each date. Here, the "date" indicates a date in the past when each medical care action has been performed, and a date in the future when each medical care action is scheduled to be performed. The "frame definition data" are defined as data, which are required to define the frame such as a size of the frame, an item name of the frame, a font for use in the display, a size of the font, text data indicating a text of comment and so on. Then, with respect to each of the frame definition files, a plurality of cell definition files are set. Each of the cell definition files stores cell definition data including at least the positional data, among the positional data, the medical care category code and the text data. Here, the "cell definition data" are defined as data, which are required to define the content to be displayed within each cell, including the positional data indicating the line and column of each cell, the medical care category code corresponding to each cell, the text data indicating the comment in text to be displayed within each cell and so on. The master file stores the medical care action appellation data indicating the appellation of the medical care action corresponding to respective one of the medical care category codes, in association with each of the medical care category codes.

In operation, at first, an arbitrary one of the frame definition files is selected through the frame selection device by an operation of an operator, such as a medical doctor, a nurse or the like. Then, by the display data generation device, the frame display data to display the frame of the table is generated on the basis of the frame definition data stored in the selected frame definition file. Along with this, by the display data generation device, each cell corresponding to respective one of the cell definition files is specified on the basis of the positional data in the cell definition data stored in each of the cell definition files set for the selected frame definition file. Then, the medical care category code, which is included in the stored cell definition data, is developed to the medical care action appellation data, which correspond to the medical care category code to be developed, with referring to the master file, and the cell content display data to be displayed in the specified each cell is generated on the basis of the developed medical care action appellation data and the text data, by the display data generation device. Then, on the basis of the generated frame display data and the generated cell content display data, the table is displayed by the display device. Next, an arbitrary one of the cells constructing the displayed table is selected through the cell selection device by an operation of the operator, such as the doctor, the nurse or the like. Then, the cell content display data is newly inputted, added, changed, modified or deleted on the display device as for the cell selected by the cell selection device, through the input device by an operation of the operator. In this manner, when the cell content display data is newly inputted, added, changed, modified or deleted by the input device, the cell definition file specified on the basis of the positional data of the selected cell is updated by the update device in correspondence with the newly inputted, added, changed, modified or deleted cell content display data.

Consequently, according to the system of the present invention, it is very convenient to refer to or input the table in which the medical care actions are arranged for each type and for each date. Further, since the table can be displayed by a desired format, the table suitable for the usage circumstance or usage object of the respective system can be displayed or printed as the occasion demands. Particularly, by simple and clear input operations e.g., newly inputting, adding, changing, modifying and deleting the data on the display device by use of the input device, the data storage content of the cell definition file or the frame definition file can be updated, which is very convenient.

In one aspect of the system of the present invention, frame title data indicating a unique title is appended to each of the frame definition files. And that, the frame selection device selects one of the frame definition files, which has a desired frame title, by searching the frame title data.

According to this aspect, the frame title data indicating a unique title is appended to each of the frame definition files. Here, as the "frame title", such a title as indicating that the pertinent frame is suitable for a specific disease, such as "schedule table for cancer", "schedule table for Alzheimer's disease" and so on, is given. Therefore, at the time of newly composing a medical care schedule and record table, it is possible to search and select one of the frame definition files, which has a desired frame title by an operation of the operator.

Consequently, it is possible to make the best use of the case data in the past etc. for the medical care schedule and record table.

In another aspect of the system of the present invention, the input device is constructed to append patient identification data, which indicate arbitrary one of a plurality of patients, to the frame definition file selected by the frame selection device. And that, the frame selection device selects one of the frame definition files for a desired patient by searching the patient identification data.

According to this aspect, the patient identification data, which indicate arbitrary one of a plurality of patients, are appended to the frame definition file selected by the frame selection device, through the input device by an operation of the operator. Therefore, at the time of referring to or re-writing the medical care schedule and record table for the pertinent patient later on, one of the frame definition files, which is related to a desired patient, can be searched and selected by an operation of the operator.

Consequently, it is possible to display the medical care schedule and record table as for the desired patient speedily even in case of coping with a great number of patients.

In another aspect of the system of the present invention, the display data generation device generates menu display data to display a menu of candidacies for newly inputting, adding, changing or modifying the cell content display data when the cell is selected by the cell selection device. And that, the input device is constructed to newly input, add, modify or change the cell content display data on the menu based on the generated menu display data and displayed on the display device.

According to this aspect, when the cell is selected by the cell selection device, the menu of candidacies for newly inputting, adding, changing or modifying the cell content display data is displayed on the display device. Here, as the menu display, a list of the medical care actions which have possibilities to be newly inputted, added, changed or modified according to the category of the medical care actions corresponding to the pertinent cell for example. Therefore, the cell content display data can be newly inputted, added, changed or modified on the menu display through the input device by an operation of the operator.

Consequently, it is possible to perform a speedy data editing operation, by newly inputting, adding, changing or modifying the data through the input device by an operation of the operator on the menu display.

In addition, without displaying this type of menu of candidacies, the system may be constructed such that the medical care category code or the text data are inputted through the input device such as the key board or the like. Here especially, in case that the medical care action appellation is inputted by use of the text data, the inputted text data are preferably converted to the medical care category code with referring to the master file so as to update the cell content display data.

In another aspect of the system of the present invention, the medical care category code comprises a computer code indicating each item chargeable by a medical insurance. The system is further provided with a calculation device for calculating a medical care insurance point for each cell on the basis of the medical care category code, which has been newly inputted, added, changed, modified or deleted, each time when the medical care category code is newly inputted, added, changed, modified or deleted by the input device, and to output medical care insurance point data. The cell definition file stores the cell definition data further including the medical care insurance point data. And that, the display data generation device generates the cell content display data on the basis of the medical care insurance point data in addition to the developed medical care action appellation data and the text data.

According to this aspect, each time when the medical care category code (e.g. the computer code) is newly inputted, added, changed, modified or deleted through the input device by an operation of the operator, the medical care insurance point for each cell is calculated on the basis of the medical care category code, which has been newly inputted, added, changed, modified or deleted, and is outputted as the medical care insurance point data, by the calculation device. Then, the cell definition data further including the medical care insurance point data are stored in the cell definition file. Further, on the basis of the medical care insurance point data, the cell content display data are generated by the display data generation device, so that the medical care insurance point data are displayed in each cell of the table displayed by the display device.

Consequently, it is very convenient when calculating or evaluating the medical care insurance reward.

In another aspect of the system of the present invention, the input device is constructed to specify at least one of the cells in the displayed table as a display object. And that, the display data generation device generates display data to display the cell definition data, which are related to the cell specified as the display object, in a format different from the table.

According to this aspect, at least one of the cells in the displayed table is selected as a display object, by an operation of the operator. Then, the cell definition data, which are related to this cell specified as the display object, are displayed in the format different from the table. Here, as the display in this different format, there area display in a list of the cell definition data related to the specified cell, a display of a magnified cell and the like, for example.

Consequently, the medical care action appellation data of various types or its detail medical care data can be displayed in a display form suitable for the respective data.

In another aspect of the system of the present invention, the input device is constructed to change the frame definition data as for the frame definition file selected by the frame selection device. And that, the display data generation device makes from a font at least one portion of display data for filling each of the cells in the table while setting a size of the font in harmonization with the size of each cell determined by the frame defined by the frame definition data, which has been changed by the input device.

According to this aspect, when the frame definition data are changed though the input device by an operation of the operator, by the display data generation device, the size of the font making the display data for filling each cell of the table is set in harmonization with the size of each cell determined by the frame defined by the frame definition data, which has been changed by the input device. As a result, the font having the size harmonized with the size of each frame of the table is always displayed by the display device.

Consequently, the table filled with the font suitable for the size of each frame can be always displayed, so that it is very easy and comfortable to watch and recognize the table.

In another aspect of the system of the present invention, the system further comprises a counter for counting the date. And that, the display data generation device generates at least one of the cell content display data and the frame display data such that one portion of graphical output related to the date corresponding to a present day is displayed in a display manner different from that of the other portion of graphical output, on the basis of the date counted by the counter.

According to this aspect of the system, the date is counted by the counter, and at least one of the cell content display data and the frame display data are generated by the display data generation device such that one portion of graphical output related to the date corresponding to a present day is displayed in a display manner different from that of the other portion of graphical output, on the basis of the date counted by the counter. Here, the different display manner may be such a display manner that the color, the brightness, the styles, the kind of lines, the concentration, the half tone meshing etc. are changed on the displayed image. Consequently, the table in which one portion of graphical output corresponding to the present day is displayed in the different display manner is outputted by the outputting device. Thus, it is possible to visually recognize at a moment notice where is the present day i.e., up to which date the medical care treatment has been performed at the present time in the table in which the items are arranged for each date.

In another aspect of the system of the present invention, a result flag, which indicates whether or not the medical care action indicated by each of the medical care category codes has been already performed, is appended to each of the medical care category codes. And that, the display data generation device generates at least one of the cell content display data and the frame display data such that one portion of graphical output related to the medical care action which has been already performed is displayed in a display manner different from that of another portion of graphical output related to the medical care action which has not been performed yet, on the basis of the result flag.

According to this aspect of the system, at least one of the cell content display data and the frame display data are generated by the display data generation device on the basis of the result flag such that one portion of graphical output related to the medical care action which has been already performed is displayed in a display manner different from that of another portion of graphical output related to the medical care action which has not been performed yet. Consequently, the table, by which it is possible to visually recognize at a moment notice whether or not each medical care action has been performed, can be graphically outputted by the display device. Further, it is also possible to visually recognize whether or not the detail medical data indicating the result of the medical care action exist logically under the medical care action appellation data, which is very convenient.

In another aspect of the system of the present invention, at least some of the medical care category codes are appended with time data indicating time of the day in addition to the date. And that, the display data generation device generates the cell content display data such that the at least some of the medical care category codes are arranged per each time of the day in each cell of the table, on the basis of the time data.

According to this aspect of the system, as for at least some of the medical care category codes to which the time data are appended, the medical care category codes are arranged per each time of the day in each cell of the table, on the basis of the time data.

Consequently, it is possible to promptly recognize the arrangement in time sequence of the medical care actions on each day, which is very convenient.

In another aspect of the system of the present invention, the cell definition data further include detail medical care data related to the medical care action indicated by respective one of the medical category codes. The input device is constructed to specify a desirable medical care action appellation among from the medical care action appellations displayed in the table by the display device. The display data generation device further generates display data to display the detail medical care data related to the medical care action appellation, which has been specified by the input device, in a predetermined format different from the table, on the basis of the detail medical care data. And that, the display device displays the generated display data in the format different from the table.

According to this aspect of the system, when a desired medical care action appellation data are inputted through the input device from among the medical care action appellation data displayed as the table, by an operation of the operator, the detail medical care data related to the specified medical care action appellation data are displayed in the predetermined format different from the table. In this case, as the format, there are a list, a graph, a chart and the like. The whole of the detail medical care data may be stored in the cell definition file. Alternatively, a specific address in an exclusive file for storing the detail medical care data may be stored as a pointer in the cell definition file, and the detail medical care data may be read out by accessing the address.

Consequently, the various information can be treated on the picture plane of the display device having the limited size, which is convenient.

In this aspect, the detail medical care data may include numerical data, which are related to a predetermined type of the medical care action, which is indicated by the respective one of the medical care category codes, and are recorded with respect to a plurality of dates. The display data generation device generates one display data to graphically output the table at one portion of an output image and generates another display data to graphically output the numerical data as a graph having a time axis corresponding to an arrangement of the dates of the table at another portion of the output image on the basis of the numerical data. And that, the display device displays the generated one and another display data.

According to this case, the display data to graphically output the table at one portion of an output image and another display data to graphically output the numerical data as a graph having a time axis corresponding to the arrangement of the dates of the table at another portion of the output image are generated on the basis of the numerical data, by the display data generation device. As a result, the table is displayed at one portion of the output image, while the graph having the time axis corresponding to the arrangement of the dates of the table is displayed at another portion of the output image.

Consequently, it is possible to visually recognize the relationship between the medical care actions, which have been performed, and the numerical data indicating the condition etc. of the body of the patient, which is very convenient.

In another aspect of the system of the present invention, the system is further provided with a communication device connectable to another medical care schedule and record aiding system through a predetermined communication path, for transmitting and receiving at least the cell definition data.

According to this aspect of the system, at least the cell definition data are transmitted and received through a predetermined communication path by the communication device, so that the cell definition data can be shared or commonly used by a plurality of medical care schedule and record aiding systems.

The above object of the present invention can be also achieved by a medical care schedule and record aiding method in the above described medical care schedule and record aiding system of the present invention. The method is provided with: a frame selection process of selecting an arbitrary one of the frame definition files; a display data generation process of (i) generating frame display data to display the frame of the table on the basis of the frame definition data stored in the selected frame definition file, (ii) specifying each cell corresponding to respective one of the cell definition files on the basis of the positional data in the cell definition data stored in each of the cell definition files set for the selected frame definition file, (iii) developing the medical care category code, which is included in the stored cell definition data, to the medical care action appellation data, which correspond to the medical care category code to be developed, with referring to the master file, and (iv) generating cell content display data to be displayed in the specified each cell on the basis of the developed medical care action appellation data and the text data; a display process of displaying the table on the display device on the basis of the generated frame display data and the generated cell content display data; a cell selection process of selecting an arbitrary one of the cells constructing the displayed table; an input process of newly inputting, adding, changing, modifying or deleting the cell content display data on the display device as for the cell selected by the cell selection process; and an update process of updating the cell definition file specified on the basis of the positional data of the selected cell, when the cell content display data is newly inputted, added, changed, modified or deleted by the input process, in correspondence with the newly inputted, added, changed, modified or deleted cell content display data.

According to the method of the present invention, in the same manner as the aforementioned system of the present invention, it is very convenient to refer to or input the table in which the medical care actions are arranged for each type and for each date. Further, the table suitable for the usage circumstance or usage object of the respective system can be displayed or printed as the occasion demands. Particularly, by simple and clear input operations e.g., newly inputting, adding, changing, modifying and deleting the data on the display device by use of the input device, the data storage content of the cell definition file or the frame definition file can be updated.

The above object of the present invention can be also achieved by a program storage device readable by the above described medical care schedule and record aiding system, tangibly embodying a program of instructions executable by the medical care schedule and record aiding system to perform method processes for aiding a preparation of medical care schedule and record. The method processes are provided with the processes of: a frame selection process of selecting an arbitrary one of the frame definition files; a display data generation process of (i) generating frame display data to display the frame of the table on the basis of the frame definition data stored in the selected frame definition file, (ii) specifying each cell corresponding to respective one of the cell definition files on the basis of the positional data in the cell definition data stored in each of the cell definition files set for the selected frame definition file, (iii) developing the medical care category code, which is included in the stored cell definition data, to the medical care action appellation data, which correspond to the medical care category code to be developed, with referring to the master file, and (iv) generating cell content display data to be displayed in the specified each cell on the basis of the developed medical care action appellation data and the text data; a display process of displaying the table on the display device on the basis of the generated frame display data and the generated cell content display data; a cell selection process of selecting an arbitrary one of the cells constructing the displayed table; an input process of newly inputting, adding, changing, modifying or deleting the cell content display data on the display device as for the cell selected by the cell selection process; and an update process of updating the cell definition file specified on the basis of the positional data of the selected cell, when the cell content display data is newly inputted, added, changed, modified or deleted by the input process, in correspondence with the newly inputted, added, changed, modified or deleted cell content display data.

According to the program storage device, such as a CD-ROM, a ROM, a DVD (Digital Video or Versatile Disk), a floppy disk or the like, of the present invention, the above described method of the present invention can be performed as the system reads and executes the program of instructions.

The nature, utility, and further features of this invention will be more clearly apparent from the following detailed description with respect to preferred embodiments of the invention when read in conjunction with the accompanying drawings briefly described below.

BRIEF DESCRIPTION OF THE DRAWINGS

FIG. 4 is a plan view showing one example of a table which is graphically outputted by the embodiment;

FIG. 5 is a plan view showing one example of a list which is graphically outputted by the embodiment;

FIG. 6 is a plan view showing another example of a table which is graphically outputted by the embodiment;

FIG. 10 is a diagram showing functions of the medical care navigation system of the embodiment.

DETAILED DESCRIPTION OF THE PREFERRED EMBODIMENT

Referring to the accompanying drawings, an embodiment of the present invention will be now explained.

Figure 1:
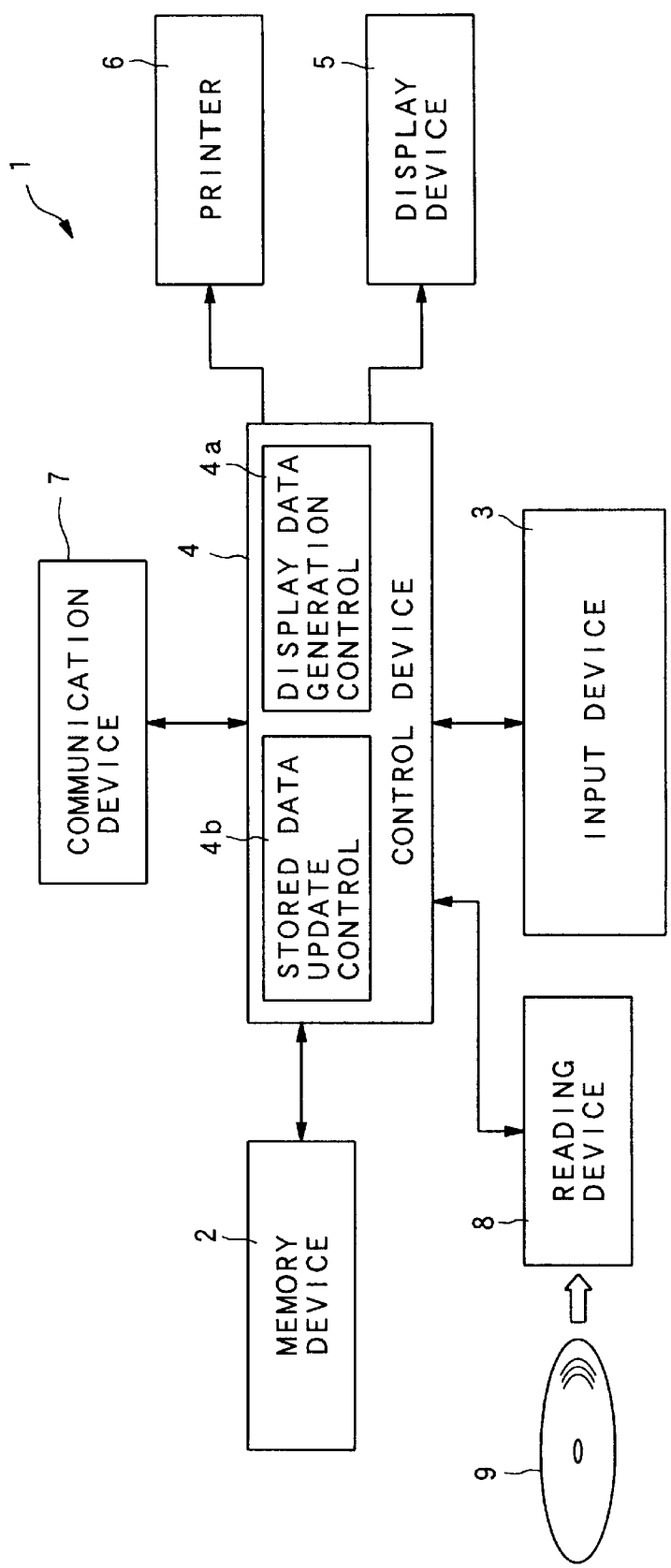
FIG. 1 is a block diagram of a medical care navigation system as an embodiment of the present invention.

FIG. 1 shows a block diagram of a medical care navigation system for navigating the staffs in the hospital e.g. the doctor, the nurse, the pharmacist and the like to the appropriate medical care, as an example of the medical care schedule and record aiding system of an embodiment of the present invention.

In FIG. 1, a medical care navigation system 1 is provided with: a memory device 2; an input device 3; a control device 4; a display device 5; a printer 6; and a communication device 7.

The memory device 2 is preferably a known large data volume memory device of randomly accessible type, such as a hard disc device, an IC (Integrated Circuit) memory, a magnetic disc device, an optical disc device or the like.

Figure 2:
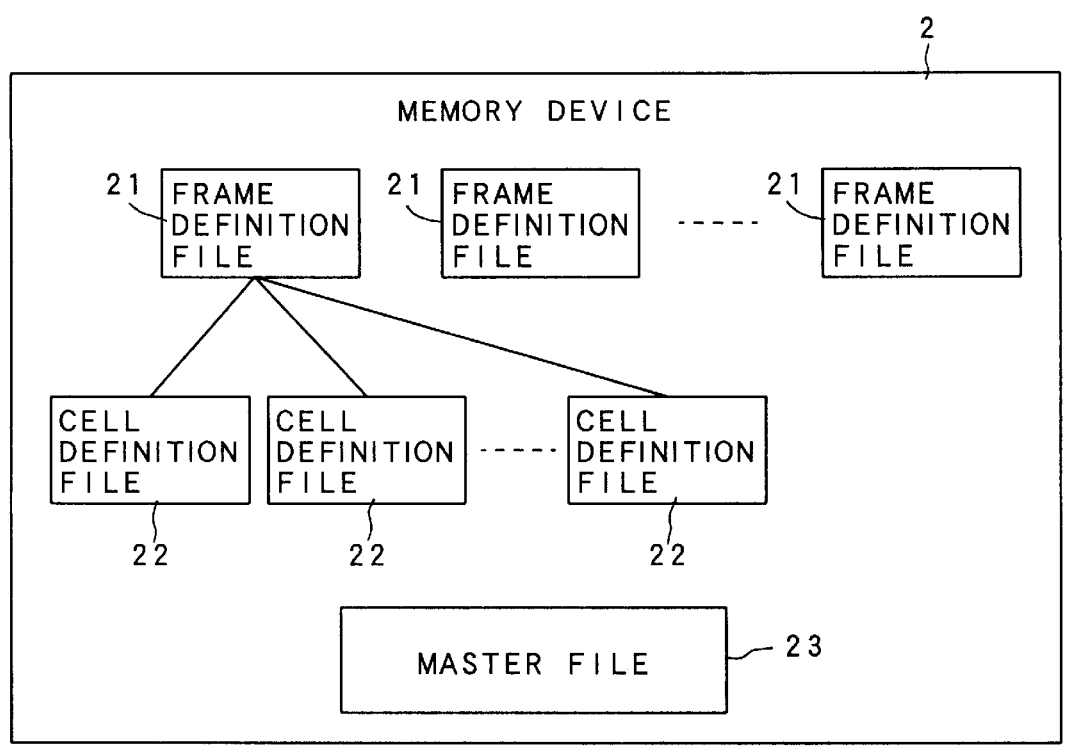
FIG. 2 is a diagram showing a file structure constituted in the memory device of the embodiment.

As shown in FIG. 2, in the memory device 2, a plurality of frame definition files 21 are logically constructed. Each of the frame definition files 21 stores frame definition data. The frame definition data define a frame of a schedule table, in which medical care actions of various types (e.g. a test, a treatment, an injection, an examination, an evaluation, a medication) are arranged for each of predetermined categories and for at least each date (or a time unit shorter than date such as an hour, a minute) related to the performance of respective one of the medical care actions. Further, in each of the frame definition files 21, a plurality of cell definition files 22 are logically constructed. Each of the cell definition files 22 stores cell definition data, for each of the cells, which are constructed as the schedule table is divided by the frame into the cells. The cell definition data include: positional data indicating a line and a column of each cell; a medical care category code corresponding to each cell among a plurality of medical category codes assigned to a plurality of medical care actions of various types respectively in advance; and text data indicating text to be displayed within each cell. Furthermore, in the memory device 2, a master file 23 is logically constructed. The master file 23 stores medical care action appellation data, which indicate each appellation (name) of the medical care actions corresponding to the plurality of medical category codes, in association with each of the medical category codes.

Here, the "frame definition data" are more concretely data, which are required to define the frame such as a size of the frame, an item name of the frame, a font for use in the display, a size of the font, text data indicating a text of comment and so on.

In the present embodiment, especially, a frame title data indicating a peculiar frame title is appended to each of the frame definition files 21, at a header portion of the frame definition file 21 for example. Here, as "the frame title", a title is preferable which indicates that the pertinent frame is suitable for a specific disease, such as "schedule table for cancer", "schedule table for Alzheimer's disease" and so on, and which is appended with the explanation for the specific disease. The input device 3, which functions as a frame selection means as described later, is adapted to select the frame definition file 21 having a desired frame title by searching the frame title data. Therefore, at the time of newly constituting a medical care schedule table for example, the frame definition file 21 having a desired frame title can be searched and selected from among a plurality of frame definition files 21, by the control device 4 in response to the operation by the doctor, the nurse or the like.

The input device 3 is, as described later in detail, adapted to append patient identification data, which indicate an arbitrary one of the patients among a plurality of patients, to the frame definition file 21, at the header portion of the frame definition file 21 for example. Then, by searching the patient identification data appended in this way, the frame definition file 21 as for the desired patient can be selected. Thus, as the patient identification data indicating the arbitrary one of the patients is appended to the frame definition file 21 related to the table displayed on the display device 5 according to the operation of the medical doctor, nurse etc., the frame definition file 21 as for the desired patient can be searched and selected from among a plurality of frame definition files 21 at the time of referring to or re-writing the medical care schedule table for the pertinent patient.

The "cell definition data" are defined here as the data, which are necessary to define the content to be displayed within each cell, including the positional data indicating the line and column of each cell, the medical care category code corresponding to each cell, the text data indicating the comment in text to be displayed within each cell, the rule data to rule or prescribe how to display the text data within each cell and so on.

The "medical care category code" is defined as a code uniquely set to each of medical care actions, and is a binary computer code for example. This code is determined in such a manner that, in case of the computer code of "0110100" for example, the upper 3 digits "011" represents an "injection" as a large category of the medical care action, and the lower 4 digits "0100" represents a "continuous infusion (drip)" as a concrete medical care action among this large category "injection". More concretely, a so-called "Rece (medical Reward Invoice)-Computer Code", which has been recently introduced in Japan and which is set for each of all items chargeable by the medical care insurance, can be utilized as this medical care category code.

In FIG. 2, the master file 23 stores a plurality of medical care action appellation data, each indicating the appellation (name) of respective one of medical care actions corresponding to a plurality of medical care category codes, in association with each of the medical care category codes. Therefore, in order to display the schedule table, the medical care category code in the cell definition file 22 can be easily and promptly developed to the corresponding medical care action appellation data, by referring to the master file 23. On the contrary to this, in case that the medical care action appellation data is changed on the schedule table, after the medical care action appellation data is converted to the corresponding medical care category code, the medical care action appellation data after the conversion can be stored into the cell definition file 22.

In addition, the medical care action indicated by the medical care category code stored in the cell definition file 22 includes the medical care actions which have been already performed in the past and the medical care actions which are scheduled to be performed in the future. A result flag indicating whether each of the medical carte actions has been already performed or not is appended to respective one of the medical care category codes. Further, detail medical care data, which accompany each medical care action indicated by respective one of the medical care category codes, are also stored in the cell definition file 22. Here, the "detail medical care data" is defined as numerical data related to each predetermined type of medical care action, such as the body temperature data, the blood pressure data, the concentration data of predetermined component in the blood and so on, which are measured every day for example.

Figure 3:
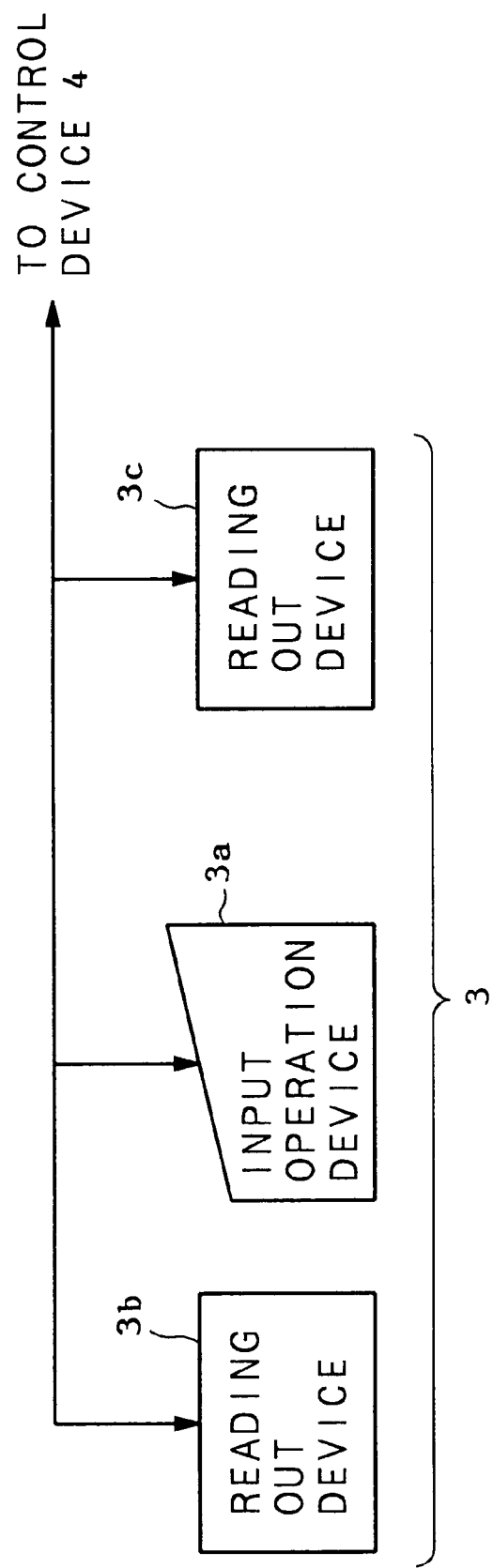
FIG. 3 is a block diagram showing a detailed construction of an input device of the embodiment.

In FIG. 3, the input device 3 is provided with an input operation device 3a such as a key board, a ten key switch, a mouse, a track ball, an input pen, an input tablet or the like, and is adapted to specify an arbitrary position on the image displayed on the display device 5. Namely, the input operation device 3a is adapted to select an arbitrary one of the frame definition files 21, and also select an arbitrary one of the cells constituting the schedule table, which is displayed on the display device 5. Such a selection of the frame definition file 21 is preferably performed by displaying a menu of the frame titles of the frame definition files 21 on the picture plane of the display device 5 and then selecting one of the displayed frame titles in the menu, by an operation of specifying the position on the menu by use of the mouse or by an operation of specifying the number on the menu by use of the key board. Further, such a selection of the cell is preferably performed by selecting one of the cells in the displayed table on the picture plane of the display device 5, by an operation of specifying the position of the cell by use of the mouse or by an operation of specifying the number of the cell by use of the key board. The input operation device 3a is adapted to newly input, add, change, modify or delete the cell content display data on the picture plane of the display device 5 as for the selected cell. In the present embodiment, especially, when the detail medical care data obtained as the result of the medical care action is inputted, the result flag, which indicates that the pertinent medical care action has been already performed, is set with respect to the medical care category code in the cell definition file 22. In the present embodiment especially, when the detail medical data, which have been obtained as a result of the medical care action, are inputted, the result flag is set ON which indicates the fact that the pertinent medical care action has been performed.

In FIG. 3, in addition to the input operation device 3a, the input device 3 is also provided with a reading out device 3b for reading out the patient identification data from a record medium to which the patient identification data are recorded. As the record medium in this case, a card type medium, on which the patient identification data are electrically, magneto-electrically, magneto-optically or optically recorded such as a magnetic card, an IC card, etc., is convenient. As the reading out device 3b, a device for electrically, magneto-electrically, magnetically, magneto-optically or optically reproducing the data in correspondence with the type of record medium is utilized. The input device 3 is further provided with a reading out device 3c for reading out the cell definition data from a record medium to which the cell definition data are recorded. In this case, as the record medium in this case, a known large data volume type record medium to which the cell category data indicating the medical care actions for each patient, each date and each type of actions for example, are electrically, magneto-electrically, magnetically, magneto-optically or optically recorded such as a magnetic disc, a magneto-optical disc, an optical disc, a ROM, an IC card, a magnetic tape, etc., may be utilized. As the reading out device 3c, a device for reading the record medium electrically, magneto-electrically, magnetically, magneto-optically or optically in correspondence with the kind of record medium is utilized.

The medical care navigation system 1 is also provided with a record medium reading device 8 such as an optical disk driver device, a floppy or flexible disk driver device and so on, and a record medium 9 readable by the record medium reading device 8, such as an optical disk, a floppy or flexible disk and so on. The record medium 9 as one example of a program storage device, tangibly embodies a program of instructions executable by the medical care navigation system 1 to perform method steps for aiding a preparation of medical care schedule and record. The program read by the record medium reading device 8 may be stored in the memory device 2, so as to speedily execute the program.

In FIG. 1 again, the control device 4 having a CPU (Central Processing Unit) is provided with a display data generation control device 4a for: generating frame display data to display a frame on the basis of the frame definition data stored in the frame definition file 21 which is selected by the input device 3; specifying each cell corresponding to respective one of the cell definition files 22 on the basis of the positional data in the cell definition data stored in the cell definition files 22 provided for the selected cell definition file 21; developing the medical care category code in the stored cell definition data 22 to the corresponding medical care action appellation data with referring to the master file 23; and generating the cell content display data to be displayed in each of the specified cells on the basis of the developed medical care action appellation data and the text data. Further, the control device 4 is provided with a stored data update control device 4b for updating the cell definition file 22 specified on the basis of the positional data of the cell selected by the input device 3 in correspondence with the cell content display data, which has been newly inputted, added, changed, modified or deleted, when the cell content display data is newly inputted, added, changed, modified or deleted by the input device 3.

The display data generation control device 4a is preferably constructed to control the display device 5 to perform the menu-display of candidacies to be newly inputted, candidacies to be added and candidacies to be changed or modified, when the cell is selected by the position specifying operation by use of the mouse etc. of the input operation device 3a. And that, the input operation device 3a is preferably constructed to newly input, add, change or modify according to the data in the displayed menu. In this case, as the menu-display, a list of the medical care actions each of which has a possibility to be newly inputted, added, changed or modified in accordance with the category of the medical care action corresponding to the pertinent cell, for example.

Alternatively or additionally, the medical care navigation system 1 may be constructed such that the medical care category code or the text data are inputted through the input operation device 3a etc., without the above mentioned menu-display. Here, especially in case of inputting the medical care action appellation by the text, the inputted text data (i.e. the medical care action appellation data) are converted to the medical care category code with referring to the master file 23 as aforementioned, so as to update it.

Further, especially in the present embodiment, it is preferable that the frame definition data as for the displayed table on the display device 5 can be changed by the input operation device 3a. In this case, the display data generation control device 4a constitutes at least one portion of the display data to be displayed in each cell of the table by a font or fonts, and sets the size of the font to be harmonized with the size of each cell which is determined according to the frame defined by the frame definition data changed by the input operation device 3a. Therefore, even if the frame is changed to one favorite for the user, the font harmonized with the displayed cell (frame) is appropriately displayed in the table, so that it is possible to prevent the font from being out of the cell and prevent the unnecessary space from being generated in the cell.

In the present embodiment, the medical care category code in the cell definition data is the computer code which indicates each item chargeable by the medical care insurance. Each time when the medical care category code is newly inputted, added, changed or deleted by the input device 3, the control device 4 calculates the medical care insurance point for each cell by a predetermined equation expressed by the rule data, which rules or prescribes the predetermined equation in advance, on the basis of the medical care category code newly inputted, added, changed, modified or deleted by the input device 3. The cell definition file 22 is constructed to further store the medical care insurance point data. On the other hand, the display data generation control device 4a controls the display device 5 to display the medical care insurance point data calculated in this manner as one portion of the cell content display data. Therefore, according to the present embodiment, by the manual operation of the operator such as the doctor, the nurse, etc., each time when the medical care category code is newly inputted, added, changed, modified or deleted, the updated medical care insurance point is automatically displayed and stored into the cell definition file 22, which is very convenient.

In FIG. 1 again, the display device 5 may be a known display device such as a CRT (Cathode Ray Tube) display device, an LCD (Liquid Crystal Display) device or the like, and is especially constructed such that an arbitrary position on its picture plane can be specified by the input device 3.

The printer 6 may be a known printer such as a laser beam printer, an ink jet printer or the like, and may be a color type or a black and white type.

The communication device 7 is constructed to perform a data communication with another medical care navigation system or the like through a telephone line, an exclusive communication line or the like. It is convenient that the frame definition file 21 or the cell definition file 22 can be shared or can be transmitted and received with respect to another medical care navigation system by use of the communication device 7. Incidentally, this kind of data sharing can be also enabled by once storing the frame definition file 21 or the cell definition file 22 stored in the memory device 2 into the floppy disk or the like, and carrying it between a plurality of medical care navigation systems.

By the medical care navigation system 1 constructed in the above explained manner, a table 10 is displayed on the picture plane of the display device 5 as shown in FIG. 4 for example.

In FIG. 4, the table 10 has a plurality of lines (horizontal rows) 11, which are divided into each type of medical care actions, and a plurality of columns (vertical rows) 12, which are divided into each date. The medical care actions of various types consisting each line 11, may be the record by the doctor or nurse, the process, the injection, the examination, the test, the evaluation, the medication, the meal (food), the practice, the monitor, the treatment, the activity restriction, the observation, the rehabilitation, the coordination, the hospitalization and the leave of hospital, the education for the family of the patient and so on. As for those items of medical care activities, an arbitrary item can be set depending upon the usage condition of the medical care navigation system 1. Since various formats each of which has a possibility to be used are stored in the frame definition file 22 shown in FIG. 2 in advance, the desired one of the formats can be selected by the input operation device 3a, which is very convenient. This selection of the format may be performed by displaying a menu for format selection on the display device 5. In this case, in addition to the medical care category code indicating each medical care action, the medical care action may be displayed on the basis of the text data in which each medical care action is expressed by the text in certain language. Especially, the cell definition data indicating the record of the doctor or nurse (i.e. the comment data) may include the text data indicating the pathobiology of the patient by the text, or the code data indicating the pathobiology of the patient by the specific code according to the predetermined rule, and further, the data in which the medical care results are expressed by the text or code data.

As shown in FIG. 4, the record of the doctor and the record of the nurse, which are recorded conventionally on different ledgers, can be displayed or printed on the same display picture plane or the same printed sheet, so that the canalization of the intentions and the team work between the doctor and the nurse can be promoted.

In the present embodiment, although the detail medical data indicating the detail record related to the medical care action of "record" in the table of FIG. 4 are not seen on the table, the detail medical data are stored in the cell definition file 22 in a form of hanging from each cell definition data in the logical data structure. For example, by clicking the mouse of the input operation device 3a of FIG. 3 on the picture plane of the display device 5 at a display position in a certain frame of the table of FIG. 4, the detail medical data corresponding to the item in the frame are displayed in the format different from this. Then, a time stamp is stamped to the medical care data and its accompanied detail medical data related to the "record" in the record of FIG. 4 each time when recording is performed by the doctor or the nurse. Namely, the date and the time of recording are recorded as the detail medical data. Thus, the doctor and the nurse can share the information in a conversation manner by use of the table.

The input operation device 3a is adapted to newly input, add, change, modify and delete the output data in each frame of the table 10 when the table 10 is displayed on the display device 5. The stored data content of the cell definition file 22 is adapted by the new cell definition data and its accompanied detail medical data under the control of the stored data update control device 4b. Because of the construction as described above, a table, which has a framework as shown in FIG. 4 and which major frames are originally blanked or which include only the medical care data indicating one standard medical care schedule initialized as the default values according to the predetermined standard, is firstly displayed on the display device 5. After that, the doctor in charge etc. can newly input the data manually by use of the input operation device 3a of FIG. 3, and can add, change, modify or delete the data manually by use of the input operation device 3a of FIG. 3, so as to make the medical care record and schedule one item by one item, which is very convenient. Further, the medical care data displayed on the table 10 can be wholly or partially replaced by the medical care data stored in the floppy disk etc. and read out by the reading out device 3c of FIG. 3, which indicate the medical care schedule appropriately applied to the patient in the past.

The medical care navigation system 1 may be provided with a timer or counter for counting the date, and the display data may be generated such that the graphically outputted portion related to the date coincident with "today" is displayed in a manner different from the other graphically outputted portion, on the basis of the date counted by the timer or counter. Here, as the display and/or print in a different manner, there are display methods of displaying or printing the image different in the brightness, the color, the style, the kind of lines, the concentration, the half-tone dot meshing etc. on the picture plane or the printed sheet.

In the present embodiment, the input operation device 3a is adapted to specify at least one cell displayed in the table (e.g. at least one of an arbitrary data and an arbitrary type in the dates and the types of actions in the table displayed on the display device 5) as the object of display. The display data generation control device 4a is adapted to generate the display data for displaying the cell definition data and its accompanied detail medical data, which are related to this specified one of the date and/or type, in the format different from that of the table, on the picture plane of the display device 5. Namely, the display data generation control device 4a is constructed to generate the display data for displaying only some portion of the medical care category data and its accompanied detail medical data, which are related to the specified data and/or type among the dates and types in the table, fully on the picture plane in a list format as shown in FIG. 5 or in a magnified manner.

The switching operation from the display of the table in FIG. 4 to the display of the list in FIG. 5 can be performed when the mouse is clicked after the cursor is moved to a desirable item (e.g. frame) in the table 10 of FIG. 4 by use of the input operation device 3a of FIG. 3. Namely, by use of the detail medical data related to the medical care category data corresponding to a desired item where the cursor is positioned on the display picture plane of FIG. 4, the list of FIG. 5 is displayed. In this case, the list of FIG. 5 may be displayed by opening a window on the table of FIG. 4. Alternatively, by omitting the display of the table shown in FIG. 4, the detail medical data display as shown in FIG. 5 or the magnified display may be directly performed.

The input operation device 3a is constructed to change the frame definition data e.g., specify the number of dates to be included in one table by the display device 5, for example. The display data generation control device 4b is constructed to make at least one portion of the display data, which fills one frame of the table by the font, and to set the size of the font in harmonization with the size of each frame in the table, which is determined according to the dates specified by the input operation device 3a. Namely, for example, if 14 days are specified as the dates included in one table such as "July $1^{st}$ to July $14^{th}$", the font size corresponding to this relatively small size of the frame is used to generate the display data. On the other hand, if 3 days are specified as the dates included in one table such as "July $1^{st}$ to July $3^{rd}$", since the frame size is rather large, the font size corresponding to this relatively large size is used to generate the display data.

In the present embodiment, the result flag is appended to the medical care category data, which indicates whether or not the medical care action indicated by the medical care category data has been already performed. The display data generation control device 4a is constructed to generate the display data such that the graphically displayed portion corresponding to the medical care action, which has been already performed, and the graphically displayed portion corresponding to the medical care action, which has not been performed yet, are displayed in a manner different from each other on the basis of the result flag. For example, the action which has not been performed yet may be displayed by use of blue colored characters, while the action which has already been performed may be displayed by use of black colored characters. Further, the medical care category data, which can be displayed in a special format different from that of the table e.g. the medical care category data which accompanies the numerical data such as the body temperature data, the blood constituent data or the like as the detail medical data, may be outputted by use of red colored characters. Other than the color, the brightness, the styles, the kind of lines, the concentration, the half tone meshing etc. may be changed on the displayed image. In this manner, by changing the display manner in accordance with the result flag, it is easy for the operator to recognize at a moment notice whether or not there exists the detail medical data as for each medical care action and whether or not the item in the table is actually completed or is in the stage of planning, which is very convenient.

FIG. 6 shows another example of the table which can be outputted by the display device 5 and the printer 6 in the present embodiment. In this case, the memory device 2 stores at least some portion of the cell definition data with respect to each time of the day in addition to the date. The display data generation control device 4a is constructed to generate the display data for graphically outputting each medical care action in the order of time of the day in each frame of the table as for at least some portion of the medical care action appellation data. Corresponding to this, the display device 5 and the printer 6 output the table 20 in which the content of each frame 21 forms a list for each time of the day as shown in FIG. 6. By this, since the medical care actions are arranged in each frame of the table in the order of time of the day, it is easy for the operator to visually recognize the medical care actions performed in one day. This is especially convenient in a case where many medical care actions to be scheduled and recorded exist in one day such as the day in the hospitalization.

Figure 7:
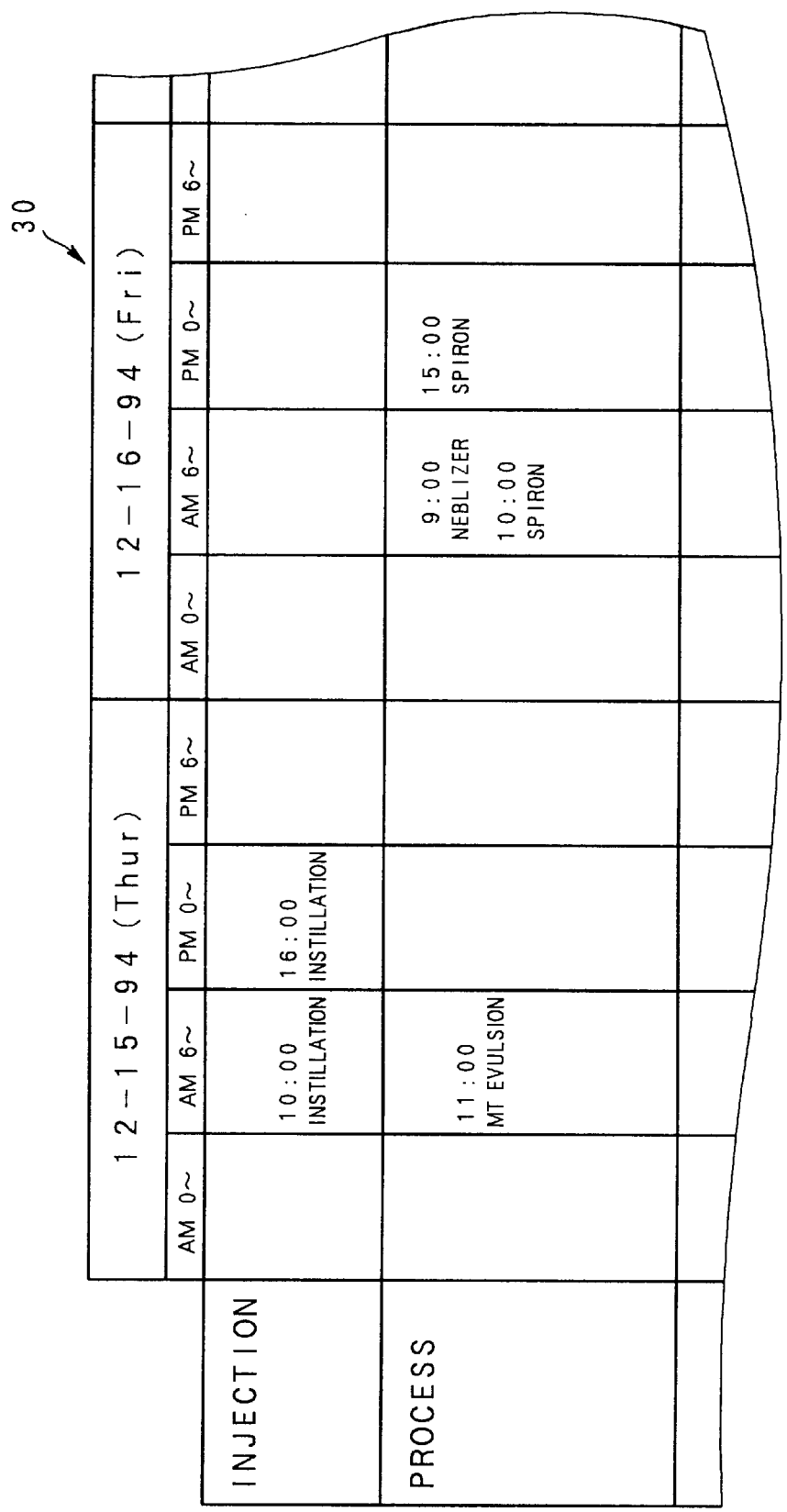
FIG. 7 is a plan view showing another example of a table which is graphically outputted by the embodiment.

FIG. 7 shows another example of the table which can be outputted by the display device 5 and the printer 6 in the present embodiment. In this case, the memory device 2 is constructed to store at least some portion of the cell definition data with respect to each time of the day in addition to the date. The display data generation control device 4a is constructed to generate the display data for graphically outputting each medical care action in a table, which columns are finely divided by a predetermined time unit in stead of just date (see FIGS. 4 and 6) in the table as for at least some portion of the medical care action appellation data. Corresponding to this, the display device 5 and the printer 6 output the table 30, in which the medical care actions in each 6 hours are put in one frame of the table and the columns are arranged every 6 hours as shown in FIG. 7. By this, if it is the case where a lot of medical care actions are to be recorded or scheduled such as the day in the hospitalization, a fine schedule for each time can be scheduled and recorded. Other than 6 hours, although a unit such as 1, 2, 3, 4, 8 or 12 hours which can easily divide 24 hours (one day) can be preferably used here, an arbitrary time unit can be used such that a time unit of long time length may be used with respect to the day time while a time unit of short time length may be used with respect to the night time. By graphically outputting the table 30 having the arrangement in the time unit, it is easy for the operator to visually recognize the medical care actions performed in one day.

Figures 8, 9:
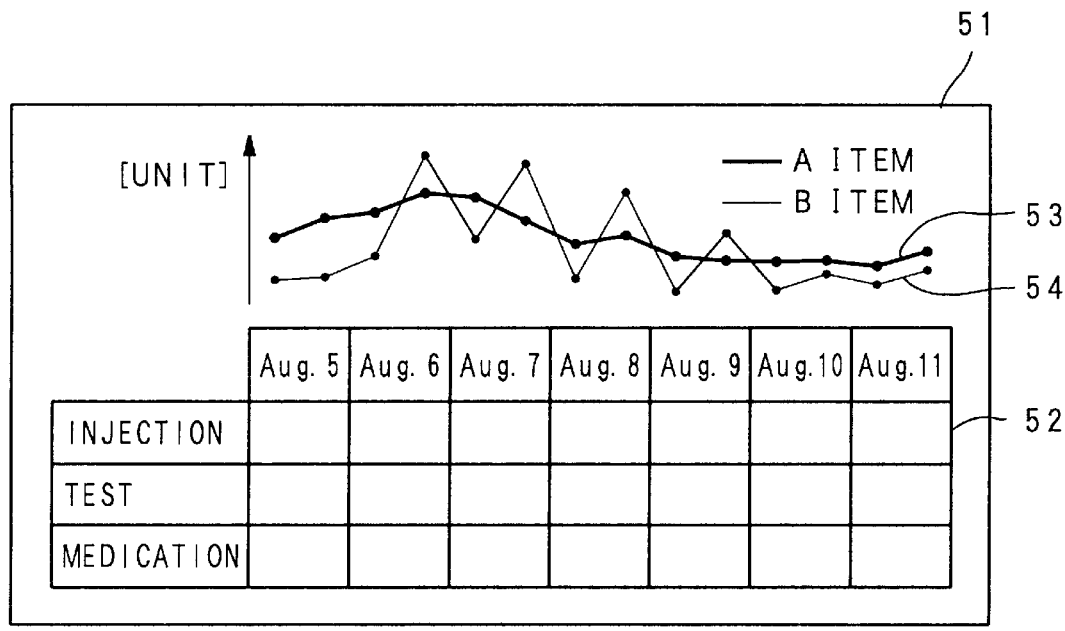
FIG. 8 is a plan view showing another example of a table which is graphically outputted by the embodiment.
FIG. 9 is a plan view showing another example of a table which is graphically outputted by the embodiment.

FIG. 8 shows another example of the table which can be outputted by the display device 5 and the printer 6 in the present embodiment. In this case, the display data generation control device 4a is constructed to generate the display data for graphically outputting in a format of a table in which the medical care action appellation data are integrated by a unit of a plurality of successive dates for at least some portion of the medical care action appellation data. Corresponding to this, the display device 5 and the printer 6 output the table 40 in which the medical care actions in each one month period are put in one frame 41 of the table and the columns are arranged ever month as shown in FIG. 8. Other than one month, although a time unit such as 3 days, one week, one year or 10 years which are easily understood, can be preferably used here, an arbitrary time unit can be used such that a short time length may be used for the time unit with respect to the period of the hospitalization while a long time length may be used for the time unit with respect to the period for the outpatient. By generating the cell definition data in correspondence with the amount of the frequency of the medical care actions, it is easy for the operator to visually recognize the aspect of the medical care actions in a long time span.

FIG. 9 shows another example of the table which can be outputted by the display device 5 and the printer 6 in the present embodiment. In this case, the detail medical data include the numerical data related to a certain medical care action which is repeatedly recorded with respect to a plurality of dates (e.g. the body temperature, the blood pressure, the specific content concentration in the blood). The display data generation control device 4a is adapted to generate the display data for graphically outputting the table 52 at one portion of the picture plane 51 of the display device 5 and at the same time graphically outputting the numerical data as a graph having the abscissa corresponding to the arrangement of the dates of the table 52 at another portion of the picture plane 51. As a result, as shown in FIG. 9, the table 52 is displayed at the lower portion of the display picture plane 51. A polygonal line graph 53 indicating the numerical data as for the A item (e.g. the body temperature) and the polygonal line graph 54 indicating the numerical data as for the B item (e.g. blood pressure), each of which have the time axis of the date of the table 52, are displayed in the upper margin of the table 52. Accordingly, since the numerical data can be shown as the graph in correspondence with the date of the table 52, it is easy for the operator to visually recognize the relationship between the medical care actions which have been performed in the past and the numerical data which indicate the body condition etc. of the patient to which the medical care actions were applied. As shown in the example of FIG. 9, if there are several data obtained by the measurements several times in one day, by drawing the graph such that the width of each frame of the table 52, which expresses one day, is converted to 24 hours, and that the upper line of the table 52 is made corresponding to the time axis of the graph, the time relationship between the numerical data and the table 52 can be still easily recognized. On the other hand, even if the numerical data do not always exist for every date, it is still possible to draw the polygonal line graph by use of the existing data and/or by interpolating the existing data.

The format information indicating the display formats of the tables such as the tables shown in FIGS. 4 to 9 as explained above, are stored in the memory device 2 in advance, so that desirable one of them can be selected by use of the menu picture plane for selecting the format, for example.

Nextly, the operation of the present embodiment will be explained in detail. The operation explained hereinbelow is performed by the medical care navigation system 1, in accordance with the program of instructions to perform the method steps for aiding the preparation of medical care schedule and record, which is recorded on the record medium 9 and is read by the record medium reading device 8. The read program may be stored in the memory device 2.

First of all, the operation for referring to the table is be explained.

When the referring operation is started, in the medical care navigation system 1, it is checked by the stored data update control device 4b whether or not there is the input of the patient identification data from the input device 3. Then there is the input from the input device 3, the frame definition file 21 corresponding to the inputted patient identification data is selected from the memory device 2. Nextly, by the display data generation control device 4a, the frame display data to display the frame are generated on the basis of the frame definition data selected in this way. Along with this, each cell corresponding to respective one of the cell definition files 22 is specified on the basis of the positional data in the cell definition data stored in the cell definition files constructed with respect to the selected frame definition file 21. Then, the medical care category code in the pertinent cell definition data is developed to the corresponding medical care action appellation data with referring to the master file 23. Then, on the basis of the developed medical care action appellation data and the text data, the cell content display data to be displayed in each of the specified cell is generated. Then, the table shown in each of FIGS. 4 to 9 for example, is displayed, on the basis of the generated frame display data and the cell content display data by the display device 5, and the referring process is ended.

Nextly, the operation for inputting (e.g., newly inputting, adding, changing, modifying or deleting) the medical care data is explained.

When the inputting operation is started, it is checked by the stored data update control device 4b whether or not there is the input of the cell definition data and its accompanied detail medical data from the input device 3. Here, one of the cells constituting the displayed schedule table is selected by the inputting operation of the operator such as the doctor, the nurse, etc., and the cell content display data as for this selected cell is newly inputted, added, changed, modified or deleted on the display device 5 through the input operation device 3a. Then, the stored content of the cell definition file 22 specified on the basis of the positional data of the selected cell is updated by the stored data update control device 4b in correspondence with the cell content display data which have been newly inputted, added, changed, modified or deleted. Then, the input process is ended.

In the above explained embodiment, the input device 3 may be constructed to input operator identification data for identifying an operator as well as the patient identification data. In this case, the stored data update control device 4b is constructed to select only the cell definition data, which indicate the medical care action of the type set in advance as the type able to be referred to by the respective operator indicated by the inputted operator identification data, from the cell definition file 22. For example, in the memory device 2, there is stored an operator table, which indicates whether or not each of the doctor, the trainee doctor, the trainee medical student, the nurse, the semi-nurse, the cook, the driver and so on is allowed to refer to the medical care data in each type of actions, so that the medical care data in the type of action able to be referred to by the pertinent operator indicated by the received operator identification data can be speedily extracted by checking this operator table.

By this construction, only the medical care data and its accompanied detail medical data, which belong to the range specified as the range able to be referred to depending on the operator category in advance, can be actually referred to, the leakage of the secret information or the infringement of the patient privacy can be efficiently prevented. In this case, the operator identification data may be inputted from the input operation device 3a, the patient identification data and the operator identification data may be inputted though the input operation device 3a, the operator identification data may be inputted through the reading out device 3b, or the patient identification data and the operator identification sate though the reading device 3b.

The medical care navigation system 1 may be connected with a plurality of other medical care navigation systems of the same type through a communication line. In this construction, the medical care data can be shared or commonly used by the medical care navigation systems. In order to make all of the medical care data coincident to each other in all of the memory devices in the medical care navigation systems, each time when the new medical care data are inputted at each of the medical care navigation systems, or each time when the data are added, changed, modified and deleted, the new medical care data are transmitted and received by the communication device 7 in each of the medical care navigation systems, so that the stored content of each memory device 2 are updated by the received medical care data. Alternatively, the stored content of each memory device 2 may be unified to the new medical care data periodically e.g. at a time of opening or closing the work ever day, or may be unified to the medical care data inputted at one medical care navigation system 1, which is predetermined to have the priority.

Finally, the functions of the medical care navigation system 1 used in the above described embodiment are conceptually indicated in FIG. 10.

In FIG. 10, the function of the medical care navigation system 1 unifies: a function of "operation on the picture plane" 13 realized by the display device 5, the input device 3 etc. shown in FIG. 1; a function of "display" 14 realized by the display device 5 etc., a function of "various system interface" 15 realized by the communication device 7, the control device 4 etc. The function of "operation on the picture plane" 13 unifies a function of "new input" 13a, a function of "add/modify input" 13b and a function of "delete" 13c. The function of "display" 14 unifies a function of "displaying the table" 14a by use of the medical care data, a function of "displaying the result" 14b by use of the medical care data and/or the detail medical data, a function of "displaying the graph" 14c for displaying the graph by use of the detail medical data, and a function of "magnification change" 14d for changing the magnification of picture plane of the display device 5.

Further, the function of "various system interfaces" 15 unifies a function of "various order" 15a for sending an order between each medical care navigation units, a function of "electronic clinical chart" 15b used by the operation unit for medical examination, and a function of "medical account" 15c used by the operation unit for account.

In this manner, since the functions are unified in the multiple layered structure, each function can be efficiently called and mutual functions organically combined to each other can be performed by the medical care navigation system 1, which is convenient.

As described above in detail, according to the present embodiments, since all of the staffs in the hospital can simultaneously see the same table, they can share the information as for the condition of the patient. Further, it is possible for each staff to suitably add, modify, change and delete the medical care schedule while watching the table, and suitably input the result data indicating the result of the medical care actions performed in accordance with the table while watching the table. Therefore, the medical care schedule which is the most suitable for each patient can be accumulated to be constructed in the memory device by the continuous data input operations of each staff i.e. by the team work of the whole staffs in the hospital, while adding some suitable adjustment toward the medical care object such as the cure of the sickness or disease. The medical care data and its accompanied detail medical data, which construct the medical care schedule scheduled in this manner, can be reserved as the record in the strict standard format.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A medical care schedule and record aiding system comprising:

a plurality of frame definition files each storing frame definition data to define a frame of a table, in which medical care actions of various types are arranged in first rows for each type of the medical care actions and in second rows orthogonal to said first rows for each date;

a plurality of cell definition files, which are set for each of the frame definition files, and each of which stores cell definition data including at least positional data, which indicates a first row and a second row of each of cells segmented by the frame of the table, among (i) the positional data, (ii) a medical care category code, which corresponds to said each of cells from among a plurality of medical care category codes respectively assigned to the medical care actions of various types in advance, and (iii) text data indicating a text to be displayed in said each of cells;

a master file for storing a plurality of medical care action appellation data, each of which indicates an appellation of a medical care action corresponding to respective one of the medical care category codes, in association with each of the medical care category codes;

a frame selection means for selecting an arbitrary one of said frame definition files;

a display data generation means for (i) generating frame display data to display the frame of the table on the basis of the frame definition data stored in said selected frame definition file, (ii) specifying each cell corresponding to respective one of said cell definition files on the basis of the positional data in said cell definition data stored in each of said cell definition files set for said selected frame definition file, (iii) developing the medical care category code, which is included in the stored cell definition data, to the medical care action appellation data, which correspond to the medical care category code to be developed, with referring to said master file, and (iv) generating cell content display data to be displayed in said specified each cell on the basis of the developed medical care action appellation data and the text data;

a display device for displaying the table on the basis of the generated frame display data and the generated cell content display data;

a cell selection device for selecting an arbitrary one of the cells constructing the displayed table;

an input device for newly inputting, adding, changing, modifying or deleting the cell content display data on said display device as for said cell selected by said cell selection device; and an update device for updating said cell definition file specified on the basis of the positional data of the selected cell, when the cell content display data is newly inputted, added, changed, modified or deleted by said input device, in correspondence with the newly inputted, added, changed, modified or deleted cell content display data.

2. A system according to claim 1, wherein frame title data indicating a unique title is appended to each of said frame definition files, and said frame selection device selects one of said frame definition files, which has a desired frame title, by searching the frame title data.

3. A system according to claim 1, wherein said input device is constructed to append patient identification data, which indicate arbitrary one of a plurality of patients, to said frame definition file selected by said frame selection device, and said frame selection device selects one of said frame definition files for a desired patient by searching the patient identification data.

4. A system according to claim 1, wherein said display data generation device generates menu display data to display a menu of candidacies for newly inputting, adding, changing or modifying the cell content display data when the cell is selected by said cell selection device, and said input device is constructed to newly input, add, modify or change the cell content display data on the menu based on the generated menu display data and displayed on said display device.

5. A system according to claim 1, wherein the medical care category code comprises a computer code indicating each item chargeable by a medical insurance, said system further comprises a calculation device for calculating a medical care insurance point for said each cell on the basis of the medical care category code, which has been newly inputted, added, changed, modified or deleted, each time when the medical care category code is newly inputted, added, changed, modified or deleted by said input device, and to output medical care insurance point data, said cell definition file stores the cell definition data further including the medical care insurance point data, and said display data generation device generates the cell content display data on the basis of the medical care insurance point data in addition to the developed medical care action appellation data and the text data.

6. A system according to claim 1, wherein said input device is constructed to specify at least one of the cells in the displayed table as a display object, and said display data generation device generates display data to display the cell definition data, which are related to the cell specified as the display object, in a format different from the table.

7. A system according to claim 1, wherein said input device is constructed to change the frame definition data as for said frame definition file selected by said frame selection device, and said display data generation device makes from a font at least one portion of display data for filling each of the cells in the table while setting a size of the font in harmonization with the size of each cell determined by the frame defined by the frame definition data, which has been changed by said input device.

8. A system according to claim 1, wherein said system further comprises a counter for counting the date, and said display data generation device generates at least one of the cell content display data and the frame display data such that one portion of graphical output related to the date corresponding to a present day is displayed in a display manner different from that of the other portion of graphical output, on the basis of the date counted by said counter.

9. A system according to claim 1, wherein a result flag, which indicates whether or not the medical care action indicated by each of the medical care category codes has been already performed, is appended to said each of the medical care category codes, and said display data generation device generates at least one of the cell content display data and the frame display data such that one portion of graphical output related to the medical care action which has been already performed is displayed in a display manner different from that of another portion of graphical output related to the medical care action which has not been performed yet, on the basis of the result flag.

10. A system according to claim 1, wherein at least some of the medical care category codes are appended with time data indicating time of the day in addition to the date, and said display data generation device generates the cell content display data such that said at least some of the medical care category codes are arranged per each time of the day in each cell of the table, on the basis of the time data.

11. A system according to claim 1, wherein said cell definition data further include detail medical care data related to the medical care action indicated by respective one of the medical category codes, said input device is constructed to specify a desirable medical care action appellation among from the medical care action appellations displayed in the table by said display device, said display data generation device further generates display data to display the detail medical care data related to the medical care action appellation, which has been specified by said input device, in a predetermined format different from the table, on the basis of the detail medical care data, and said display device displays the generated display data in the format different from the table.

12. A system according to claim 11, wherein the detail medical care data include numerical data, which are related to a predetermined type of the medical care action, which is indicated by the respective one of the medical care category codes, and are recorded with respect to a plurality of dates, said display data generation device generates one display data to graphically output the table at one portion of an output image and generates another display data to graphically output the numerical data as a graph having a time axis corresponding to an arrangement of the dates of the table at another portion of the output image on the basis of the numerical data, and said display device displays the generated one and another display data.

13. A system according to claim 1, further comprising a communication device connectable to another medical care schedule and record aiding system through a predetermined communication path, for transmitting and receiving at least the cell definition data.

14. A medical care schedule and record aiding method in a medical care schedule and record aiding system, said system comprising: a plurality of frame definition files each storing frame definition data to define a frame of a table, in which medical care actions of various types are arranged in first rows for each type of the medical care actions and in second rows orthogonal to said first rows for each date; a plurality of cell definition files, which are set for each of the frame definition files, and each of which stores cell definition data including at least positional data, which indicates a first row and a second row of each of cells segmented by the frame of the table, among (i) the positional data, (ii) a medical care category code, which corresponds to said each of cells from among a plurality of medical care category codes respectively assigned to the medical care actions of various types in advance, and (iii) text data indicating a text to be displayed in said each of cells; and a master file for storing a plurality of medical care action appellation data, each of which indicates an appellation of a medical care action corresponding to respective one of the medical care category codes, in association with each of the medical care category codes, said method comprising the processes of:

a frame selection process of selecting an arbitrary one of said frame definition files;

a display data generation process of (i) generating frame display data to display the frame of the table on the basis of the frame definition data stored in said selected frame definition file, (ii) specifying each cell corresponding to respective one of said cell definition files on the basis of the positional data in said cell definition data stored in each of said cell definition files set for said selected frame definition file, (iii) developing the medical care category code, which is included in the stored cell definition data, to the medical care action appellation data, which correspond to the medical care category code to be developed, with referring to said master file, and (iv)

generating cell content display data to be displayed in said specified each cell on the basis of the developed medical care action appellation data and the text data;

a display process of displaying the table on a display device on the basis of the generated frame display data and the generated cell content display data;

a cell selection process of selecting an arbitrary one of the cells constructing the displayed table;

an input process of newly inputting, adding, changing, modifying or deleting the cell content display data on said display device as for said cell selected by said cell selection process; and an update process of updating said cell definition file specified on the basis of the positional data of the selected cell, when the cell content display data is newly inputted, added, changed, modified or deleted by said input process, in correspondence with the newly inputted, added, changed, modified or deleted cell content display data.

15. A program storage device readable by a medical care schedule and record aiding system, tangibly embodying a program of instructions executable by said medical care schedule and record aiding system to perform method processes for aiding a preparation of medical care schedule and record, said system comprising: a plurality of frame definition files each storing frame definition data to define a frame of a table, in which medical care actions of various types are arranged in first rows for each type of the medical care actions and in second rows orthogonal to said first rows for each date; a plurality of cell definition files, which are set for each of the frame definition files, and each of which stores cell definition data including at least positional data, which indicates a first row and a second row of each of cells segmented by the frame of the table, among (i) the positional data, (ii) a medical care category code, which corresponds to said each of cells from among a plurality of medical care category codes respectively assigned to the medical care actions of various types in advance, and (iii) text data indicating a text to be displayed in said each of cells; and a master file for storing a plurality of medical care action appellation data, each of which indicates an appellation of a medical care action corresponding to respective one of the medical care category codes, in association with each of the medical care category codes, said method processes comprising the processes of:

a frame selection process of selecting an arbitrary one of said frame definition files;

a display data generation process of (i) generating frame display data to display the frame of the table on the basis of the frame definition data stored in said selected frame definition file, (ii) specifying each cell corresponding to respective one of said cell definition files on the basis of the positional data in said cell definition data stored in each of said cell definition files set for said selected frame definition file, (iii) developing the medical care category code, which is included in the stored cell definition data, to the medical care action appellation data, which correspond to the medical care category code to be developed, with referring to said master file, and (iv) generating cell content display data to be displayed in said specified each cell on the basis of the developed medical care action appellation data and the text data;

a display process of displaying the table on a display device on the basis of the generated frame display data and the generated cell content display data;

a cell selection process of selecting an arbitrary one of the cells constructing the displayed table;

an input process of newly inputting, adding, changing, modifying or deleting the cell content display data on said display device as for said cell selected by said cell selection process; and an update process of updating said cell definition file specified on the basis of the positional data of the selected cell, when the cell content display data is newly inputted, added, changed, modified or deleted by said input process, in correspondence with the newly inputted, added, changed, modified or deleted cell content display data.

* * * * *